United States Patent [19]

Smith

[11] Patent Number: 4,476,976
[45] Date of Patent: Oct. 16, 1984

[54] STENCILLING DEVICE

[75] Inventor: Dwight Smith, Harbor City, Calif.

[73] Assignee: Marvin Elkins, San Diego, Calif.

[21] Appl. No.: 486,325

[22] Filed: Apr. 19, 1983

[51] Int. Cl.³ .................... B65D 25/08; B32B 29/00
[52] U.S. Cl. ................................ 206/219; 206/221;
206/440; 206/484; 101/125; 101/128.21;
383/38; 383/103; 427/272
[58] Field of Search ............... 206/219, 264, 221, 484,
206/440, 441; 383/103, 38; 101/125, 128.21;
427/272

[56] References Cited

U.S. PATENT DOCUMENTS

| | | | |
|---|---|---|---|
| 516,469 | 3/1894 | Bradley | 427/272 |
| 1,265,989 | 5/1918 | Becher | 101/128.21 |
| 1,781,834 | 11/1930 | D'Autremont | 101/128.21 |
| 2,517,430 | 8/1950 | Hensel et al. | 427/272 |
| 2,651,255 | 9/1953 | Wallich | 101/125 |
| 3,074,544 | 1/1963 | Bollmeier et al. | 206/219 |
| 3,749,620 | 7/1973 | Montgomery | 206/219 |
| 4,180,621 | 12/1979 | Maynard et al. | 101/128.21 |
| 4,374,869 | 2/1983 | Dorey et al. | 427/272 |
| 4,402,402 | 9/1983 | Pike | 206/221 |

FOREIGN PATENT DOCUMENTS

| | | | |
|---|---|---|---|
| 78932 | 2/1955 | Denmark | 101/128.21 |
| 2107795 | 2/1971 | Fed. Rep. of Germany | 206/484 |

*Primary Examiner*—William T. Dixson, Jr.
*Assistant Examiner*—Brenda J. Ehrhardt
*Attorney, Agent, or Firm*—Edward A. Sokolski

[57] ABSTRACT

A compartmented pouch has two or more sealed compartments formed therein, these compartments being separated from each other by a breakaway partition. One of the compartments has a stencil formed therein which may be in the form of holes punched in one wall of the compartment arranged to form a desired marking image, which may be letters, numerals or symbols. In lieu of punched holes, the images may be formed by slots in this compartment wall. Removable tape is placed over the holes or slots. One of two fluid components is placed in one compartment and another of two fluid components is placed in another compartment which may or may or not be the compartment having the images formed therein; these two components forming an etchant or marking material when combined together. Pressure is exerted on one of the compartments to force the fluid therein against the breakaway septum or partition causing the partition to break, such that the fluid passes into the second compartment to mix with the other fluid, thereby forming the etchant or marking medium. The tape covering the holes or slotted portions forming the marking image is removed and the stencil is placed against the surface to be marked, the etchant or marking medium being permitted to pass through the holes or slots in the stencil and onto the surface to be marked. In another embodiment, a single fluid may be employed, which is contained in one of the compartments.

11 Claims, 6 Drawing Figures

STENCILLING DEVICE

This invention relates to a method and apparatus for stencilling markings on objects, and more particularly to such a device employing a compartmentalized pouch having a compartment containing an etching or marking medium or such a device containing a different fluid in each of two or more compartments which are joined together to form the marking medium.

The marking of objects with identification markings which may be in the form of numbers, letters or symbols, is used extensively for security purposes. In achieving the desired end result, it is highly desirable to employ a marking medium in the form of an etchant or the like which etches the identification symbols into a surface of the object in a manner such that it cannot be readily erased or removed. Effective etchants for metal and glass and removal-resistant paint generally contain substances which can cause injury to the user's skin or eyes. Such materials must therefore be very carefully handled and limited for use by personnel having adequate protection, as well as some skill in their handling. This makes the marking process somewhat more expensive than to be desired, and obviates its use except to specially trained personnel. U.S. Pat. No. 2,517,430, issued Aug. 1, 1950, to Hensel et al., describes a typical prior art chemical etching technique.

The method and apparatus of the present invention obviates the aforementioned shortcomings of the prior art in providing a sealed packet containing the fluids needed for etching or painting symbols on a surface which can be employed by an untrained person and without the use of any special protective clothing or gloves.

The improvement is achieved in the present invention by employing a compartmentalized pouch having a plurality of compartments separated by breakaway sealing partitions. One of the compartments may contain a first fluid, while an adjacent compartment may contain a second fluid which, when combined with the first, forms an active etching or painting substance. In another embodiment of the invention, a single active fluid may be contained in one of the compartments. The second compartment may also have a stencil forming the identification letters, symbols or markings to be placed on a surface of the object to be marked, this stencil being formed by holes punched through the compartment wall or slots formed in such wall. The stencil is covered over a tape so that the substance is not released therefrom until the tape is removed and the stencil placed on the surface to be marked. In one embodiment of the invention, one of the fluids forming the etchant or marking substance is contained in the same compartment having the stencil formed thereon, while in another embodiment three compartments are employed, two of the compartments containing the fluids forming the marking substance, while the third compartment has the stencil formed therein. In this second embodiment, the fluids are mixed together in one of the first two compartments and, after mixed to form the marking substance, the fluid is forced through the breakaway sealing divider into the stencilled compartment.

It is therefore an object of this invention to provide an improved device and technique for placing identification markings on objects.

It is a further object of this invention to minimize the hazards involved in etching markings onto the surfaces of objects.

It is still another object of the invention to lessen the cost involved in placing identification markings on objects.

It is still a further object of this invention to provide a simple device and technique for marking objects which can be employed by unskilled personnel with minimal hazard of injury.

Other objects of this invention will become apparent as the description proceeds in connection with the accompanying drawings of which:

Figure 3:
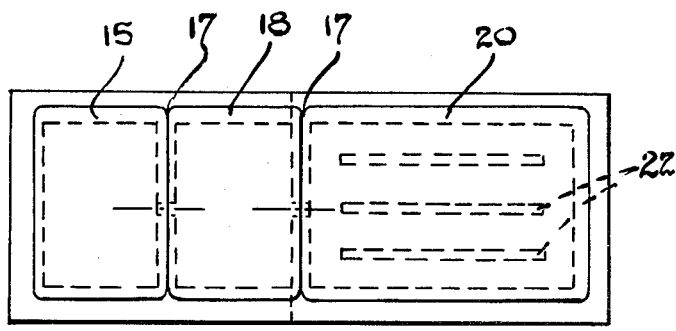
FIG. 3 is a top plan view of a second embodiment of the invention.
Figure 1:
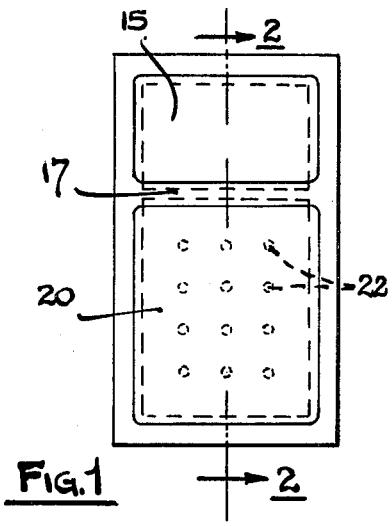
FIG. 1 is an exploded perspective view of a first embodiment of the invention.
Figure 2:
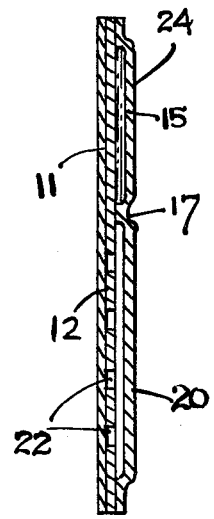
FIG. 2 is a cross-sectional view taken along the plane indicated by 2—2 in FIG. 1.

Referring now to FIGS. 1 and 2, a first embodiment of the invention is illustrated. A pouch member has a first compartment 15 and a second compartment 20 separated by a breakaway seal or septum 17. Typical materials which may be employed for the pouch are 50-gauge polyester film, 0.0015 aluminum foil or 0.002 polypropylene film. The breakaway seal 17 between the compartments may be fabricated by heat sealing the pouch material sufficiently to form a wall between the compartments which will separate the fluids but which will give way when the compartment walls are compressed. Depending upon the material used, various amounts of heating will be required as is well known in the art. A stencil 22 is formed in the lower wall 12 of compartment 20, this stencil being formed by punched holes or slots incised in wall 12. A sealing tape 11 is removably adhered to wall 12 to cover up the stencil, this layer being removed when the etchant or other marking medium has been squeezed into compartment 20 and is ready for use in marking the object. Wall 12 is preferably coated with a suitable adhesive. The marking substance may be premixed and placed in compartment 15, or if desired to keep the substance inert until it is ready for use as an etchant, one of two substances to be combined to form the marking medium is placed in compartment 15 and the other is placed in compartment 20, the two substances being mixed together by squeezing the top wall 24 of compartment 15 to force the fluid through breakaway sealing partition or septum, breaking the septum with the pressure applied thereto and permitting the fluid thus to enter compartment 20 and mix with the other fluid to form the active marking substance.

Various examples of implementations of the invention to form a marking medium are as follows:

EXAMPLE I

A mixture of commercial hydrofluoric acid containing 55% by weight of polyvinyl alcohol of the molecular weights and residual acetate composition commercially designated as Gelvatol 20.60, manufactured by Monsanto Corporation was employed. The material was stored in compartment 15 and forced into compartment 20 when stencilling was desired, this material being employed to stencil onto a sheet of safety glass. The stencil was left on the glass for 15 minutes and then removed, the pattern of the stencil being etched into the glass to a depth of 0.003 inches.

EXAMPLE II

A mixture of ferric chloride and water, available commercially from Phillip Hunt Chemical Company under the label PF Etchant, was admixed with the polyvinyl alcohol of Example I and placed in compartment 15. The material in compartment 15 was squeezed through breakway sealing septum 17 into compartment 20. The tape 11 was removed and the stencil placed on a surface of "1019" steel. After 15 minutes, at room temperature—20° C., the stencil was removed and the image of the stencil was found to have been etched into the steel to a depth of 0.004 inches.

EXAMPLE III

A two-component paint, available commercially as NAZDAR gloss black, available from Nazdar Company, Chicago, Ill. was employed, the "A" component of the paint being placed into compartment 15, while the "B" component of the paint was placed into compartment 20. Pressure was exerted on top wall 24 of compartment 15, rupturing breakaway partition 17 and permitting the material in compartment 15 to enter compartment 20. The two components were thoroughly mixed by pushing down on the top wall 27 of compartment 20 in a back and forth rocking action. Tape 11 was removed and the material placed against an aluminum surface to be etched. The stencil was immediately removed and the paint allowed to set.

Figure 4:
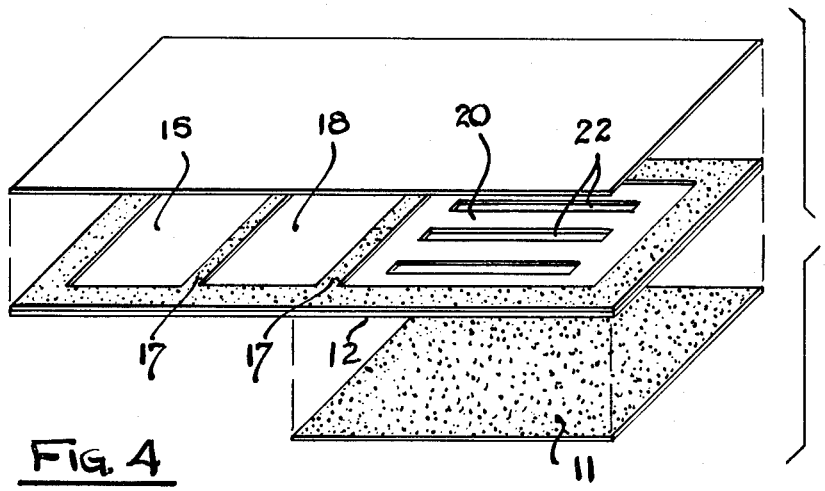
FIG. 4 is an exploded view of the second embodiment.

Referring now to FIG. 4, a second embodiment of the invention is illustrated. In this embodiment, three compartments are employed, the compartments, as in the previous embodiment, being separated from each other by a breakaway sealing septum. First compartment 15 has one of the two fluids contained therein, while compartment 18 has the other of the fluids to be mixed with the first fluid to form the marking substance. Compartment 20 has the stencil 22 on its bottom surface, this stencil being sealed by a tape 11 as in the first embodiment. Compartments 15, 18 and 20 are separated from each other by breakway sealing partition 17, as in the first embodiment. The fluid in compartment 15 is squeezed out of this compartment into compartment 18 where the two fluids are mixed to form the marking substance. When the materials have been thoroughly mixed, the mixture in compartment 18 is squeezed through breakaway partition 17 into compartment 20. The material in compartment 20 is then used to etch the desired surface, as in the previous embodiment.

Figure 5:
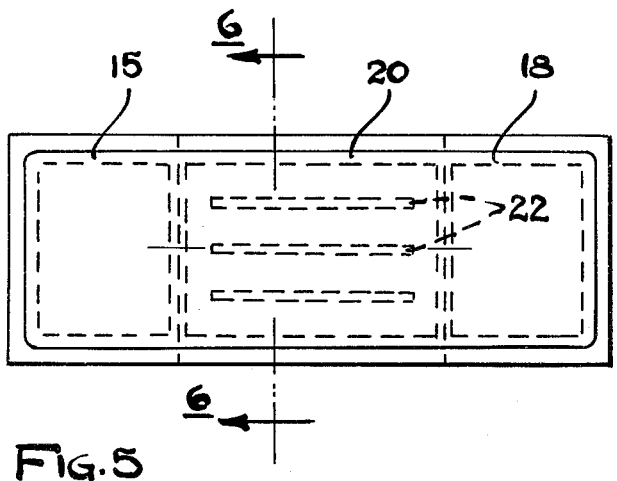
FIG. 5 is a top plan view of a third embodiment of the invention.
Figure 6:
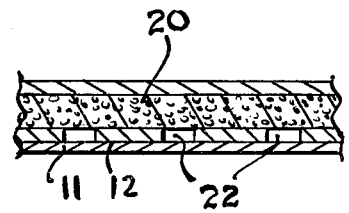
FIG. 6 is a cross-section view taken along the plane indicated by 6—6 in FIG. 5.

Referring now to FIG. 5, a further embodiment of the invention is illustrated. This embodiment is similar to that of FIG. 4 except for the fact that compartments 15 and 18, rather than being adjacent to each other, are on opposite ends of compartment 20. In this embodiment, the fluids in compartments 15 and 18 are squeezed into compartment 20 where the mixing thereof is achieved. Otherwise, this embodiment is the same as that of FIG. 4.

The device and technique of the present invention thus can be effectively used for a number of applications by relatively inexperienced personnel. Such applications include the etching of windows and metal parts; the permanent painting of objects made of a variety of different materials, such as plastic, metal glass; the use of the fluid as a transdermal medication; the use of the fluid as a spot test reagent for the identification of metal alloys; the use of the fluid as an antibiotic for testing the susceptibility of an organism; etc.

While the invention has been described and illustrated in detail, it is to be clearly understood that this is intended by way of illustration and example only and is not to be taken by way of limitation, the spirit and scope of this invention being limited only by the terms of the following claims.

I claim:

1. A compartment pouch for use in placing a fluid onto the surface of an object comprising:
   at least two sealed compartments formed in said pouch,
   a breakaway partition forming a sealing separator between said compartments,
   a first one of said compartments having a surface thereof stencilled to form an opening,
   removable tape means placed on the stencilled surface, and
   a fluid placed in a second one of said compartments,
   wherein when said second one of said compartments is squeezed, the pressure imparted to the fluid therein breaks the breakaway partition permitting the fluid to enter said first one of said compartments, whereby with the tape means removed from the stencilled surface and the stencilled surface placed against the surface of the object to receive the fluid the fluid passes through the stencilled surface onto the surface of the object.

2. The pouch of claim 1 wherein said one of said surfaces is stencilled in the form of a predetermined image to be marked on the surface of the object, said fluid being a marking fluid, whereby said image is marked on the surface of the object when the fluid passes through the stencilled surface.

3. The pouch of claim 2 wherein there are two fluids which are admixed with each other to form the marking fluid, one of said fluids being initially contained within each of said two compartments.

4. The pouch of claim 2 wherein a third compartment is formed in said pouch, said third compartment containing a first fluid to be admixed with the fluid in said second one of said compartments to form the marking fluid.

5. The pouch of claim 4 wherein the third compartment is adjacent to said second compartment.

6. The pouch of claim 4 wherein said third compartment is adjacent to said first compartment and on a side thereof opposite to said second compartment.

7. The pouch of claim 2 wherein the marking fluid is a chemical etchant.

8. The pouch of claim 3 wherein the marking fluid is a two-component paint.

9. The pouch of claim 1 wherein said fluid is a transdermal medication.

10. The pouch of claim 1 wherein said fluid is a spot test reagent for identifying metal alloys.

11. The pouch of claim 1 wherein the fluid is an antibiotic.

* * * * *